United States Patent
Mourelle Mancini et al.

(10) Patent No.: US 6,894,076 B2
(45) Date of Patent: May 17, 2005

(54) ESTERS DERIVED FROM (RR,SS)-2-HYDROXYBENZOATE OF 3-(2-DIMETHYLAMINOMETHYL-1-HYDROXYCYCLOHEXYL)PHENYL

(75) Inventors: Marisabel Mourelle Mancini, Barcelona (ES); Elisabet De Ramon Amat, Barcelona (ES); Juan Huguet Clotet, Sant Joan Despi (ES)

(73) Assignee: Vita-Invest, S.A., Sant Joan Despi (ES)

( * ) Notice: Subject to any disclaimer, the term of this patent is extended or adjusted under 35 U.S.C. 154(b) by 30 days.

(21) Appl. No.: 10/169,177

(22) PCT Filed: Dec. 26, 2000

(86) PCT No.: PCT/ES00/00486

§ 371 (c)(1),
(2), (4) Date: Jun. 27, 2002

(87) PCT Pub. No.: WO01/49650

PCT Pub. Date: Jul. 12, 2001

(65) Prior Publication Data

US 2003/0100598 A1 May 29, 2003

(30) Foreign Application Priority Data

Dec. 30, 1999 (ES) .......................................... 200000060

(51) Int. Cl.⁷ .......................... C07C 69/78; C07C 69/88; A61K 31/235
(52) U.S. Cl. .......................... 514/532; 514/544; 560/37; 560/42; 560/106; 548/300.1
(58) Field of Search ............................ 560/42, 37, 106; 514/506, 532, 544

(56) References Cited

U.S. PATENT DOCUMENTS 3,652,589 A   3/1972   Flick ................... 260/326.5 M
5,733,936 A   3/1998   Buschmann et al. ........ 514/646
6,455,585 B1 * 9/2002  Del Castillo Nieto et al. ... 514/533

FOREIGN PATENT DOCUMENTS

EP   0753506   1/1997
GB   997399    7/1965
NL   6610022   2/1967
WO   0027799   11/1999

OTHER PUBLICATIONS

Flohé, L. et al. "Clinical Study on the Development of Dependency After Long–Term Treatment with Tramadol". Arzneim.–Forsch. Drug Res. 29 (1), Heft 1a (1978), pp. 213–217.

Flick, K. et al. "Studies on Chemical Structure and Analgetic Activity of Phenyl Substituted Aminomethylcyclohexanoles", Arzneim.–Forsch. Drug Res. 28 (I), Heft 1 a (1978), pp. 107–113.

Yanagita, T. "Drug Dependence Potential of 1–(m–Methoxyphenyl)–2–(dimethylaminomethyl)–cyclohexan–1–of Hydrochloride (Tramadol) Tested in Monkeys"–Arzneim.–Forsch. Drug. Res. 28 (I), Heft 1a (1978), pp. 158–163.

Poulsen, Lars et al. "The Hypoalgesic Effect of Tramadol in Relation to CYP2D6". *Clinical Pharmacology & Therapeutics*, vol. 60, No. 6, pp. 636–644.

Eddy, Nathan B. et al. "Synthetic Analgesics. II. Dithienylbutenyl–and Dithienylbutylamines", pp. 385–393.

Matthiesen, T. et al. "The Experimental Toxicology of Tramadol: An Overview". *Toxicology Letters* 95 (1998), pp. 63–71.

Lintz, W. et al. "Biotransformation of Tramadol in Man and Animal". Arzneim.–Forsch./Drug Res. 31 (II), Nr. 11 (1981), pp. 1932–1943.

Vogel, W. et al. "The Effect of Tramadol, a New Analgesic, on Respiration and Cardiovascular Function", Arzneim.–Forsch. Drug Res. 28 (I), Heft 1a (1978), pp. 183–186.

Arend, L et al. "Tramadol and Pentazocin in a Doubleblind Crossover Comparison". Arzneim.–Forsch. Drug Res. 28 (I), Heft 1a (1978), pp. 199–208.

* cited by examiner

*Primary Examiner*—Joseph K. McKane
*Assistant Examiner*—Golam M M Shameem
(74) *Attorney, Agent, or Firm*—Steinberg & Raskin, P.C.

(57) ABSTRACT

New esters derived from (RR, SS)-3-(2-dimethylaminomethyl-1-hydroxycyclohexyl)phenyl 2-hydroxybenzoate, analog to Tramadol, a process for obtaining them and the use of these compounds for the production of a medicament with analgesic properties.

These new products of general formula (I) exhibit an analgesic activity higher than that of tramadol.

10 Claims, No Drawings

ESTERS DERIVED FROM (RR,SS)-2-HYDROXYBENZOATE OF 3-(2-DIMETHYLAMINOMETHYL-1-HYDROXYCYCLOHEXYL)PHENYL

This application is a 371 of PCT/ES00/004896 filed Dec. 26, 2000.

FIELD OF THE INVENTION

The present invention refers to new esters derived from (RR, SS)-3-(2-dimethylaminomethyl-1-hydroxycyclohexyl) phenyl 2-hydroxybenzoate, analog to Tramadol. The obtained compounds exhibit an analgesic activity higher than that of tramadol.

BACKGROUND OF THE INVENTION

Treatment of pain is of foremost importance in the field of medicine. The pharmacological agents currently used for the treatment of pain may be included, for the most part, in two large groups: opioid compounds and nonsteroidal anti-inflammatory drugs (NSAIDs). The NSAIDs are only useful in the case of light to moderate pain; severe pain has been traditionally treated with opioid compounds. However, said opioid compounds present a series of undesired side effects, such as constipation, respiratory depression, and tolerance and addiction liability.

U.S. Pat. No. 3,652,589 describes a class of analgesic compounds with a structure of substituted cycloalkanol phenol ethers having an amino group of alkaline character in the cycloalkyl ring. Among them, the compound (1R,2R or 1S,2S)-2-[(dimethylamino)methyl]-1-(3-methoxyphenyl) cyclohexanol, commonly known as Tramadol, may be thrown into relief, and it is specifically claimed in said patent.

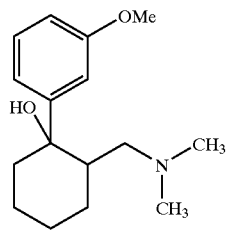

Tramadol

A series of products derived from the previous ones, in which dehydration in the cycloalkanol ring together with demethylation of the 3-methoxyl on the phenyl ring has taken place, having the structure:

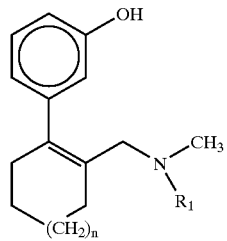

are disclosed in the Dutch Patent NL 6,610,022.

This patent also describes products derived from those of the aforementioned US Patent, in which the methoxyl group at the 3-position on the phenyl ring has been demethylated. Namely, products having the structure:

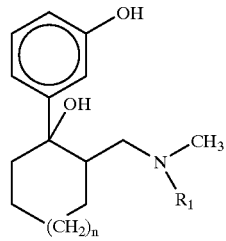

Among the products described in this patent O-demethyltramadol is included, which compound has been described as one of the metabolization products of Tramadol (Von W. Lintz and col. Arzneim-Forsch (*Drug Res*) 31 (II); 1932–43 (1981). To its (+) isomer has been attributed the analgesic activity of Tramadol (Lars Poulsen and col. Clin. Pharmacol. Ther (St. Louis) 1996, 60 (6), 636–644). Even so, data do not exist on the clinical use of the metabolite O-demethyltramadol.

More recently, in EP 753506, new O-demethylsubstituted, 1-halogenated and/or 3-cyclohexyl substituted derivates of tramadol, have been described.

Tramadol possesses an opioid agonistic effect. However, the clinical practice with Tramadol indicates that in spite of this fact, it does not possess some of the typical side effects of the opioid agonists, such as respiratory depression (W. Vogel and col. Arzneim. Forsch (*Drug Res*) 28 (I), 183 (1978)), constipation (I. Arend and col., *Arzneim. Forsch* (*Drug Res*) 28 (I), 199 (1978), tolerance (L. Flohe et al., *Arzneim. Forsch* (*Drug Res*) 28 (I), 213 (1978)) and possibility of abuse (T. Yenagita et al., *Arzneim. Forsch* (*Drug Res*) 28 (I), 158 (1978)). Some specific side effects of Tramadol, caused when it is rapidly injected by the intravenous route (i.v.), such as suffocations and sweating, have been detected.

Another of the drawbacks shown by Tramadol is its short duration of action (T. Matthiesen, T. Wohrmann, T. P. Coogan, H. Uragg. "The experimental toxicology of tramadol: an overview". Toxicology Letters, 95, 63–71, (1998)).

Because of the previous backgrounds, new compounds with an improved analgesic activity still are of interest.

DESCRIPTION OF THE INVENTION

The present invention refers to new derivates of (RR,SS)-3-(2-dimethylaminomethyl-1-hydroxycyclohexyl)phenyl 2-hydroxybenzoate, analog to Tramadol.

The analgesic activity of these compounds has turned out to be higher than that of Tramadol.

In particular, the present invention describes and claims the products of the general formula (I), their salts and optical isomers, as well as a process for the preparation thereof. The present invention also refers to the use of these compounds for the production of a medicament intended for treatment of pain.

The products of the present invention are represented by the following general formula (I):

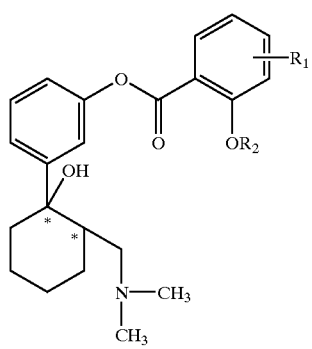

*Indicates possibility of asymmetrical carbons wherein:

R$_1$ is halogen, optionally substituted C$_1$–C$_6$ alkyl, OR$_3$, NO$_2$ or optionally substituted aryl, where R$_3$ is C$_1$–C$_6$ alkyl.

R$_2$ is H or CH$_3$CO—.

Preferably, R$_1$ is halogen, such as F, Cl, Br, halosubstituted phenyl, or hydro(C$_1$–C$_6$ fluoroakyl).

Particularly, the preferred compounds of the present invention are:

(RR-SS)-2-Acetoxy-4-trifluoromethyl-benzoic acid 3-(2-dimethylaminomethyl-1-hydroxy-cyclohexyl)-phenyl ester (RR-SS)-2-Hydroxy-4-trifluoromethyl-benzoic acid 3-(2-dimethylaminomethyl-1-hydroxy-cyclohexyl)-phenyl ester (RR-SS)-4-Chloro-2-hydroxy-benzoic acid 3-(2-dimethylaminomethyl-1-hydroxy-cyclohexyl)-phenyl ester (RR-SS)-2-Hydroxy-4-methyl-benzoic acid 3-(2-dimethylaminomethyl-1-hydroxy-cyclohexyl)-phenyl ester (RR-SS)-2-Hydroxy-4-methoxy-benzoic acid 3-(2-dimethylaminomethyl-1-hydroxy-cyclohexyl)-phenyl ester (RR-SS)-2-Hydroxy-5-nitro-benzoic acid 3-(2-dimethylaminomethyl-1-hydroxy-cyclohexyl)-phenyl ester (RR-SS)-2',4'-Difluoro-3-hydroxy-biphenyl-4-carboxylic acid 3-(2-dimethylaminomethyl-1-hydroxy-cyclohexyl)-phenyl ester The compounds of general formula (I) may be obtained by means of the following procedures, also within the scope of the present invention.

DESCRIPTION OF THE METHODS

Method A

The compounds of general formula (I) of the present invention may be obtained by means of a general procedure characterized in reacting a compound of the formula (II) with the corresponding acid or acid derivate of the general formula (III):

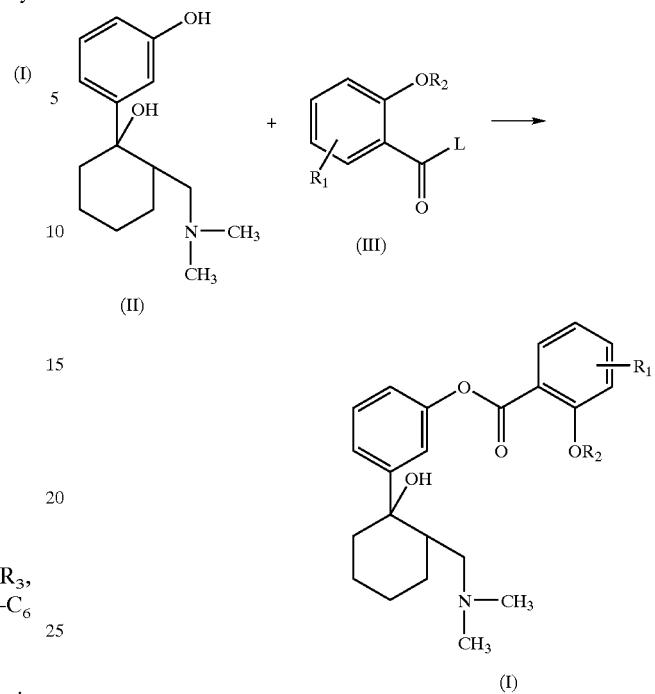

wherein R$_1$ and R$_2$ have the above defined meaning, and L=OH, halogen,

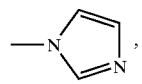

O—R$_4$ or —CO—R$_5$, where

R$_4$=C$_1$–C$_6$ alkyl, phenyl, optionally substituted phenyl, and

R$_5$ Alkyl, a phenyl ring optionally substituted with one or more substituents, or a heterocyclic ring optionally substituted with one or more substituents.

Preferably, L is OH or halogen.

The reaction is carried out in an inert solvent, such as dichloromethane, tetrahydrofuran, acetonitrile, 1,2-dichloroethane, ethyl acetate, dimethoxyethane or dioxane, preferably dichloromethane or tetrahydrofuran, at temperatures ranging from −20° C. to 120° C., preferably from 0° C. to 35° C., to obtain compounds of higher purity, and preferably in the presence of a condensation promoting agent to accelerate the reaction, such as carbonyldiimidazole, dicyclohexylcarbodiimide, triethylamine ethylchloroformate, triethylamine benzotriazoletosylate or diethylchlorophosphate, preferably carbonyldiimidazole or dicyclohexylcarbodiimide.

The compounds of formula (II) are obtained according to the methods described in the literature (NL 6610022 or Flick et al., *Arzneim. Forsch/Drug Res.* (1978), 28 (I), 107–113).

Method B

This method consists in subjecting a compound of general formula (Ia) wherein R$_2$=CH$_3$CO to a hydrolysis reaction in an acidic medium to obtain a compound of general formula (Ib) in which R$_2$=H:

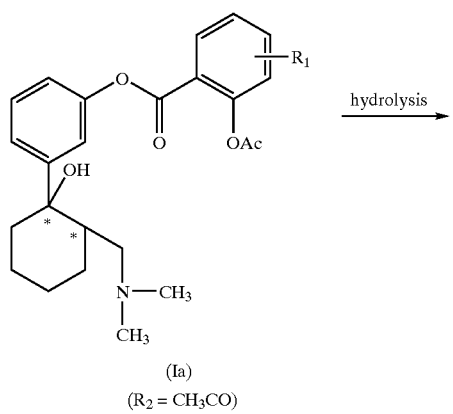

(Ia)
(R₂ = CH₃CO)

hydrolysis

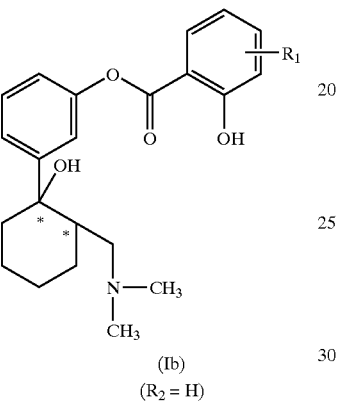

(Ib)
(R₂ = H)

wherein $R_1$ has the above defined meaning.

Next, the methods used for ascertaining the pharmacological activity of the compounds are described.
Analgesic Activity Assays
Hot-Plate Method The method used is the one described by Eddy N. B. and Leimbach D. (J. Pharm. Exp. Ther. 107: 385–393, 1953). The analgesic effect of the products was assessed by analyzing the behavior of animals on a hot surface maintained at 55° C.±1° C.

Male Swiss mice weighing 20–25 g were used. The test compounds were administered, by the oral route, 1 hour before beginning the test.

The method consisted in placing the animals on a hot plate, while maintaining them in a 25 cm diameter and 21 cm height Plexiglas cylinder, and determining the time that they take in jumping off the hot surface. The animals were selected before the beginning of the test so that those animals that remained more than 10 seconds without jumping were not included in the group that would receive treatment.

After the administration of the product under study, the test was repeated, the maximal permanence time on the hot plate being measured yet again. Those animals that did not jump lapsed 60 seconds were removed from the plate in order to avoid damage to the animal, and they were taken as being 100% protected.

The results were expressed as percent increment in the time (t) of jump, which was calculated as follows:

$$10\% \text{ increm. } t \text{ jump} = \frac{(t \text{ jump treated} - t \text{ jump basal})}{t \text{ jump basal}} \times 100$$

It is an object of the present invention the use of the compound of the general formula (I) for the production of a medicament intended for the treatment of pain. Likewise, it is also an object of the present invention a pharmaceutical composition, which comprises said compound of the general formula (I) together with a pharmaceutically acceptable excipient, for the treatment of pain.

EXPERIMENTAL

Next, the following illustrative examples are set forth, but they are not to be construed as limitative of the scope of the invention:

SYNTHESIS EXAMPLES

Example No. 1

(RR-SS)-2-Acetoxy-4-trifluoromethyl-benzoic acid 3-(2-dimethylaminomethyl-1-hydroxy-cyclohexyl)-phenyl Ester

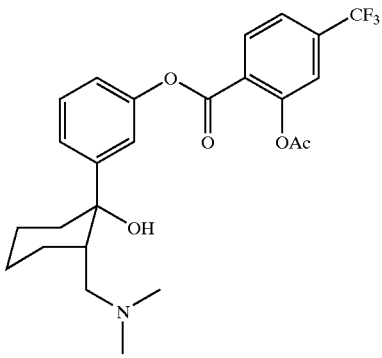

To a solution of 15.0 g (60.5 mmol) 4-trifluoromethylacetylsalicylic acid in 150 ml anhydrous tetrahydrofuran 9.3 g (57.4 mmol) carbonyldiimidazole was added, at room temperature, under an inert atmosphere. After thirty minutes, 13.1 g (52.6 mmol) 3-(2-dimethylaminomethyl-1-hydroxycyclohexyl)phenol was added. The resulting solution was maintained at room temperature for 3 days. The mixture was added onto a $NaHCO_3$ aqueous solution at pH 8 and it was extracted with dichloromethane (3×50 ml). The pooled organic extracts were dried over $Na_2SO_4$, filtered and concentrated at reduced pressure to give a residue which was purified by column chromatography on silica gel (eluent: 9:1 dichloromethane/acetone and increasing amounts of acetone), whereby yielding 20 g of the title compound as an oil.

$^1$H-NMR (CDCl₃): 1.20–2.25 (m, 16H) including a 2.15 (s, 6H); 2.30 (s, 3H), 2.45 (dd, 1H); 7.08 (m, 1H); 7.15–7.50 (m, 5H); 8.35 (m, 1H).

Example No. 2

(RR-SS)-2-Hydroxy-4-trifluoromethyl-benzoic acid 3-(2-dimethylaminomethyl-1-hydroxy-cyclohexyl)-phenyl ester

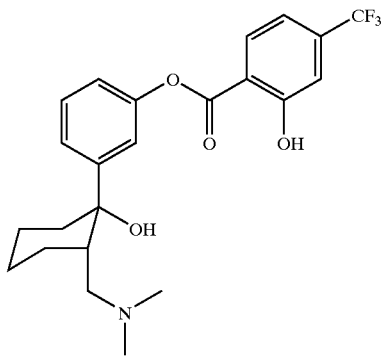

The compound of Example 1 was dissolved in 600 ml isopropanol and 25 ml 35% hydrochloric acid. The resulting solution was stirred for 16 hours at 40° C. The isopropanol was evaporated, the residue was dissolved in 100 ml dichloromethane, and it was added onto 100 ml of a NaHCO₃ aqueous solution at pH 8. Extraction of the product was carried out, and the aqueous phase was washed with fresh dichloromethane portions (2×50 ml). The pooled organic extracts were dried over Na₂SO₄, then filtered and concentrated at reduced pressure. The resultant crude product was purified by column chromatography on silica gel (eluent: dichloromethane/acetone 9:1 and increasing amounts of acetone), whereby 12.4 g (57%) of the title compound were obtained as a white foam. ¹H-NMR (CDCl₃): 1.20–2.30 (m, 16H) including a 2.15 (s, 6H); 2.45 (dd, 1H); 7.08 (m, 1H); 7.15–7.35 (m, 2H); 7.45 (m, 3H); 8.20 (m, 1H); 10.50 (br. s, 1H).

Example No. 3

(RR-SS)-4-Chloro-2-hydroxy-benzoic acid 3-(2dimethylaminomethyl-1-hydroxy-cyclohexyl)-phenyl ester

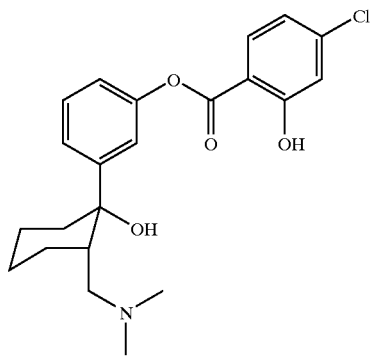

To a solution of 10.0 g (58.0 mmol) 4-chlorosalicylic acid in 150 ml anhydrous tetrahydrofuran 8.9 g (54.9 mmol) carbonyldiimidazole was added at room temperature and under an inert atmosphere. After thirty minutes, 12.6 g (50.6 mmol) 3-(2-dimethylaminomethyl-1-hydroxycyclohexyl) phenol was added. The resulting solution was maintained at room temperature for 3 days. The mixture was added onto a NaHCO₃ aqueous solution at pH 8, and it was extracted with dichloromethane (3×50 ml). The pooled organic extracts were dried over Na₂SO₄, then filtered and concentrated at reduced pressure. The resulting residue was purified by column chromatography on silica gel (eluent: dichloromethane/acetone 9:1 and increasing amounts of acetone), whereby 12.2 g (66%) of the title compound as a white foam were obtained.

¹H-NMR(CDCl₃): 1.20–2.20 (m, 16H) including a 2.12 (s, 6H); 2.45 (dd, 1H); 6.95 (dd, 1H); 7.05 (m, 2H); 7.43 (m, 3H); 8.05 (d, 1H); 10.60 (br. s, 1H).

Example No. 4

(RR-SS)-2-Hydroxy-4-methyl-benzoic acid 3-(2-dimethylaminomethyl-1-hydroxy-cyclohexyl)-phenyl ester

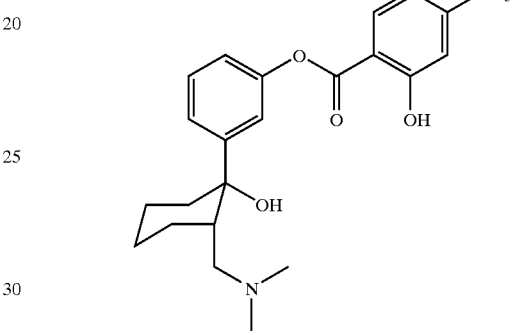

Operating in a similar way to that described to prepare the compound of Example 3 and starting from 10.0 g (65.7 mmol) 4-methylsalicylic acid, 10.0 g (61.7 mmol) carbonyldiimidazole, 14.3 g (57.4 mmol) 3-(2-dimethylaminomethyl-1-hydroxycyclohexyl)phenol and 165 ml anhydrous tetrahydrofuran, and after column chromatography on silica gel (eluent: 9:1 dichloromethane/acetone and increasing amounts of acetone), 14.6 g (66%) of the title compound was obtained as a white foam.

¹H-NMR(CDCl₃): 1.20–2.60 (m, 20H) including a 2.15 (s, 6H) and a 2.20 (s, 3H); 6.80 (m, 2H); 7.05 (m, 1H); 7.45 (m, 3H); 7.95 (d, 1H); 10.55 (s, 1H).

Example No. 5

(RR-SS)-2-Hydroxy-4-methoxy-benzoic acid 3-(2-dimethylaminomethyl-1-hydroxy-cyclohexyl)-phenyl ester

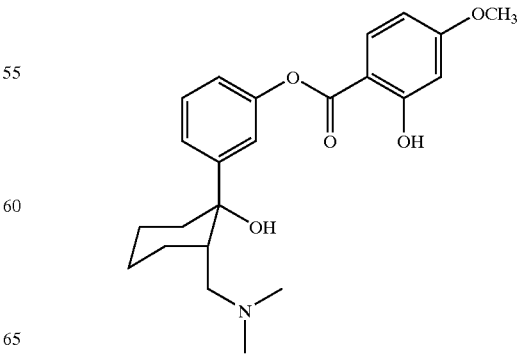

Operating in a similar way to that described to prepare the compound of Example 3 and starting from 10.0 g (59.5 mmol) 4-mehoxysalicylic acid, 9.1 g (56.2 mmol) carbonyldiimidazole, 12.9 g (51.8 mmol) 3-(2-dimethylaminomethyl-1-hydroxycyclohexyl)phenol and 150 ml anhydrous tetrahydrofuran, and after column chromatography on silica gel (eluent: 9:1 dichloromethane/acetone and increasing amounts of acetone), 13.7 g (66%) of the title compound was obtained as a white foam.

$^1$H-NMR(CDCl$_3$): 1.20–2.30 μm, 16H) including a 2.15 (s, 6H); 2.45 (dd, 1H); 3.85 (s, 3H); 6.55 (m, 2H); 7.07 (m, 1H); 7.40 (m, 3H); 7.95 (d, 1H); 10.75 (s, 1H).

Example No. 6

(RR-SS)-2-Hydroxy-5-nitro-benzoic acid 3-(2dimethylaminomethyl-1-hydroxy-cyclohexyl)-phenyl ester

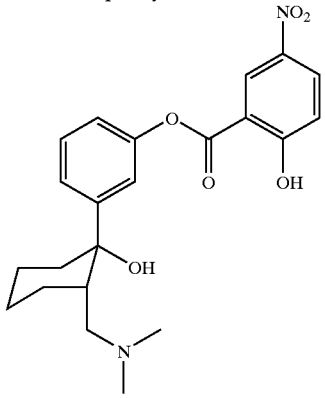

Operating in a similar way to that described to prepare the compound of Example 3 and starting from 10.0 g (54.6 mmol) 5-nitrosalicylic acid, 8.3 g (51.2 mmol) carbonyldiimidazole, 11.9 g (47.8 mmol) 3-(2-dimethylaminomethyl-1-hydroxycyclohexyl)phenol and 135 ml anhydrous tetrahydrofuran, and after column chromatography on silica gel (eluent: 1:1 dichloromethane/acetone and increasing amounts of acetone), 326 mg (2%) of the title compound was obtained as a yellow solid.

$^1$H-NMR(CDCl$_3$): 1.20–2,30 (m, 16H) including at 2,15 (s, 6H); 2.45 (dd, 1H); 7.00–7.25 (m, 2H); 7.45 (m, 3H); 8.40 (dd, 1H); 9.05 (d, 1H).

Example No. 7

(RR-SS)-2',4'-Difluoro-3-hydroxy-biphenyl-4-carboxylic acid 3-(2-dimethylaminomethyl-1-hydroxy-cyclohexyl)-phenyl ester

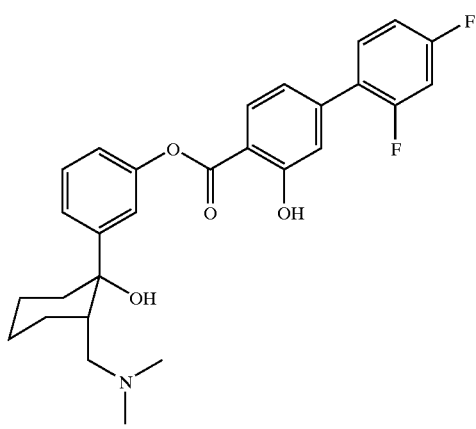

Operating in a similar way to that described in Example 3 and starting from 5.0 g 2',4'-difluoro-3-hydroxy-biphenyl-4-carboxylic acid, 3.5 g carbonyldiimidazole, 5.0 g 3-(2-dimethylaminomethyl-1-hydroxycyclohexyl)phenol and 50 ml anhydrous tetra-hydrofuran, and after column chromatography on silica gel, 4,1 g of the title compound was obtained as a white foam.

$^1$H-NMR(CDCl$_3$): 1.20–2.30 (m, 16H) including at 2.15 (s, 6H); 2.45 (dd, 1H); 6.85–7.55 (m, 9H); 7.70 (m, 1H); 8.22 (d, 1H); 10.60 (br. s, 1H).

Pharmacological Results

In the following Table 1, the pharmacological activity results for several examples of the product of the invention are shown, as well as for Tramadol. The results are expressed as percent increment in the response time in the hot plate test.

As it can be seen, the compounds of the invention present activities up to three times higher than that of tramadol.

Analgesic Activity of the Products in the Hot Plate Test in Mice

TABLE 1

| PRODUCT<br>80 μmol/kg p.o. | Percent increment<br>response time |
| --- | --- |
| Tramadol | 218 |
| EXAMPLE 1 | 710 |
| EXAMPLE 2 | 724 |
| EXAMPLE 3 | 400 |
| EXAMPLE 4 | 525 |
| EXAMPLE 5 | 688 |
| EXAMPLE 6 | 661 |
| EXAMPLE 7 | 686 |

What is claimed is:

1. Compound of general formula (I):

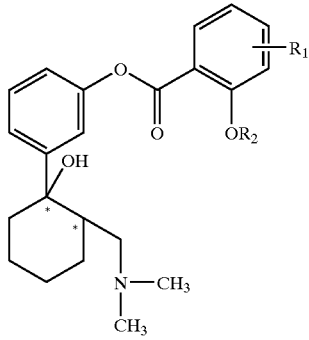

wherein: R$_1$ is halogen, optional substituted C$_1$–C$_6$ alkyl, OR$_3$, NO$_2$ or optionally substituted aryl, where R$_3$ is C$_1$–C$_4$ alkyl, R$_2$ is: H or CH$_3$ CO; and the salts and optical isomers thereof.

2. A compound according to claim 1, characterized in that $R_1$ is halogen, such as F, Cl, Br, halosubstituted phenyl or hydro ($C_1$–$C_6$ fluoroalky).

3. Compound as claimed in claim 1, characterized in that it is selected from one of the following:

(RR-SS)-2-Acetoxy-4-trifluoromethyl-benzoic acid 3-(2-dimethylaminomethyl-1-hydroxy-cyclohexyl)-phenyl ester;

(RR-SS)-2-Hydroxy-4-trifluoromethyl-benzoic acid 3-(2-dimethylaminomethyl-1-hydroxy-cyclohexyl)-phenyl ester;

(RR-SS)-4-Chloro-2-hydroxy-benzoic acid 3-(2-dimethylaminomethyl-1-hydroxy-cyclohexyl)-phenyl ester;

(RR-SS)-2-Hydroxy-4-methyl-benzoic acid 3-(2-dimethylaminomethyl-1-hydroxy-cyclohexyl)-phenyl ester;

(RR-SS)-2-Hydroxy-4-methoxy-benzoic acid 3-(2-dimethylaminomethyl-1-hydroxy-cyclohexyl)-phenyl ester;

(RR-SS)-2-Hydroxy-5-nitro-benzoic acid 3-(2-dimethylaminomethyl-1-hydroxy-cyclohexyl)-phenyl ester;

(RR-SS)-2', 4-Difluoro-3-hydroxy-biphenyl-4-carboxylic acid 3-(2-dimethylaminomethyl-1-hydroxy-cyclohexyl)-phenyl ester.

4. A process for obtaining a compound of general formula (I):

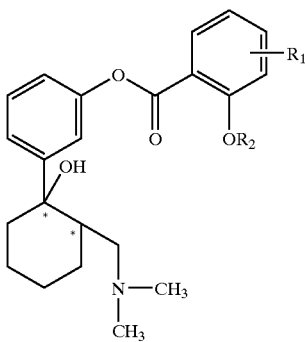

as claimed in claim 1, characterised in that a compound of formula (II);

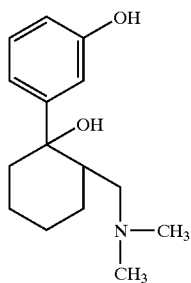

is reacted with a compound of general formula (III);

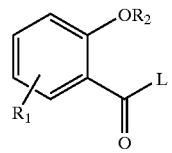

wherein $R_1$y $R_2$ have the same meaning as above, and L=OH, halogen

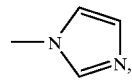

O—$R_4$ or —CO—$R_5$, where $R_4$=$C_1$–$C_4$ alkyl, phenyl, optionally substituted phenyl, and $R_5$=Alkyl, a phenyl ring optionally substituted with one or more substituents, or a heterocyclic ring optionally substituted with one or more substituents, in an inert solvent, at temperatures ranging from −20° C. to 120° C.

5. A process according to claim 4, characterized in that a condensation promoting agent is added.

6. A process according to claim 4, characterized in that said inert solvent is selected from dichloromethane, tetrahydrofuran, acetonitrile, 1,2-dichloroethane, ethyl acetate, dimethoxyethane or dioxane, preferably dichloromethane or tetrahydrofuran.

7. A process according to claim 5, characterized in that said condensation promoting agent is selected from carbonyldiimidazole, dicyclohexylcarbodiimide, triethylamine ethylchloroformate, triethylamine benzotriazoletosylate or diethylchlorophosphate, preferably carbonyldiimidazole or dicyclohexylcarbodiimide.

8. A process according to claim 4, characterized in that said temperature range is from 0° and 35° C.

9. A method for treatment of pain which comprises administering to a human being in need of said treatment an effective dose of a compound of general formula (I) according to claim 1.

10. A pharmaceutical composition, which comprises a compound of general formula (I) according to claim 1 and a pharmaceutically acceptable excipient, for the treatment of pain.

* * * * *